(12) United States Patent
Baekelmans et al.

(10) Patent No.: US 7,442,392 B2
(45) Date of Patent: Oct. 28, 2008

(54) PESTICIDES

(75) Inventors: Ivo Baekelmans, Beniarda (ES); Ron Herbert Brown, Calcot (GB); Irene Mueller-Harvey, Emmer Green (GB)

(73) Assignee: Pharming Ltd., West Midlands (GB)

( * ) Notice: Subject to any disclaimer, the term of this patent is extended or adjusted under 35 U.S.C. 154(b) by 0 days.

(21) Appl. No.: 10/588,044

(22) PCT Filed: Feb. 7, 2005

(86) PCT No.: PCT/GB2005/000425

§ 371 (c)(1),
(2), (4) Date: Dec. 22, 2006

(87) PCT Pub. No.: WO2005/077188

PCT Pub. Date: Aug. 25, 2005

(65) Prior Publication Data

US 2007/0248699 A1      Oct. 25, 2007

(30) Foreign Application Priority Data

Feb. 7, 2004    (GB) ................. 0402728.0

(51) Int. Cl.
*A61K 36/00*    (2006.01)
(52) U.S. Cl. ...................... 424/725; 424/405
(58) Field of Classification Search .......... None
See application file for complete search history.

(56) References Cited

U.S. PATENT DOCUMENTS

2001/0009903 A1* 7/2001 Niwa ..................... 514/25

FOREIGN PATENT DOCUMENTS

| JP | 8133923 | A | * | 5/1996 |
| JP | 9002913 | A | * | 1/1997 |
| JP | 9227396 | A | * | 9/1997 |
| JP | 2001-122717 | | | 5/2001 |
| WO | WO 00/07437 | A1 | * | 2/2000 |
| WO | WO 02/078451 | A1 | * | 10/2002 |
| WO | WO 02/094005 | A2 | * | 11/2002 |

OTHER PUBLICATIONS

"nematode." Grolier Multimedia Encyclopedia. 2007. Grolier Online. Nov. 26, 2007. <http://gme.grolier.com/cgi-bin/article?assetide=0205770-0>.*
Miyakodo et al., J. Pesticide Sci., 10: 101-106 (1985).*

* cited by examiner

*Primary Examiner*—Susan C Hoffman
(74) *Attorney, Agent, or Firm*—Leydig, Voit & Mayer, Ltd.

(57) ABSTRACT

The invention provides the use of loquat kernel to kill, inactivate or repel pests, in particular nematodes. Also provided is a method of killing, inactivating or repelling nematodes, which method comprises providing loquat kernel and applying the loquat kernel to the nematodes or to an area where the nematodes are likely to exist or to an area to where the nematodes are expected to move. The invention further provides a pesticide comprising loquat kernel and a pesticidally acceptable solvent, carrier, excipient or diluent; and a method of producing a pesticide, which method comprises providing ground, chopped, freeze dried or spray dried loquat kernel.

23 Claims, 1 Drawing Sheet

PESTICIDES

The present invention relates to the use of loquat kernel to kill, inactivate or repel pests, and in particular as a nematicide, i.e. a composition that kills nematodes, and more particularly as a nematicide that selectively kills plant parasitic nematodes. The invention also relates to methods of killing nematodes and to pesticide compositions and their methods of manufacture.

Nematodes are a type of worm like organism. There are different trophic groups of nematodes: fungus feeding, bacteria feeding, predatory and plant parasitic. Plant parasitic nematodes, such as root knot nematodes, are pests because they cause plants to stunt, wilt and/or yellow, often with galls developing over the roots of the plant, due to the feeding of the nematodes on the roots of the plants. Plants that are particularly vulnerable to plant parasitic nematodes include banana, capsicum, carrot, celery, cucurbits, beans, egg fruit, ginger, grape, kiwi fruit, strawberry, lettuce, carnation, chrysanthemum, rose, papaw, passion fruit, pineapple, peach, pumpkin, nectarine and tomato.

There is therefore a need for nematicides to control plant parasitic nematodes; in particular for nematicides that selectively destroy plant parasitic nematodes over other nematodes.

The loquat (*Eriobotrya japonica*) is a fruit of the family Rosaceae. The family Rosaceae also includes the fruits of the genus *Prunus*, which include almonds, apricots, peaches, plums, nectarines and cherries. The loquat is also known as the nispero and references hereinafter to the loquat should therefore be read accordingly.

The loquat is classified as being a fruit of the type "pome"; pomes are fleshy fruits having a thin skin, which consist of enlarged receptacle tissue enclosing the ovary and seeds. Other pomes include apple, pear and quince, although the seeds of the loquat are very large (ca 1-3 cm diameter) compared to apple or pear seeds.

The leaves, kernel and fruit of loquat are known for their medicinal uses; in particular the fruit is said to act as a sedative and to relieve coughing and vomiting whilst its leaves and kernel contain laetrile, which is believed by some to have anti-cancer properties. There has not, until now, however, been any teaching regarding the use of the loquat in pesticidal applications.

The present invention provides, in a first aspect, the use of loquat kernel to kill, inactivate or repel pests. In one embodiment, the kernel is used as a pesticide.

Preferably, the loquat kernel is used to kill, inactivate or repel nematodes. In a particularly preferred embodiment, the use of loquat kernel as a nematicide is provided.

It has been identified by the present inventors that the loquat kernel can effectively be used in the killing, inactivation, and/or repulsion of pests, in particular nematodes.

In particular, the invention provides the use of loquat kernel as a nematicide for plant parasitic nematodes, preferably as a selective nematicide for plant parasitic nematodes.

As can be seen from the Examples, selective killing of plant parasitic nematodes can surprisingly be achieved by the application of loquat kernel.

In particular, the use of loquat kernel as a selective treatment for nematodes over fungi is provided. As can be seen from the Examples, loquat kernel selectively acts as a nematicide; it does not act as a fungicide.

The kernel may be used in any suitable form; in particular it may be provided in ground, chopped, freeze dried or spray dried form or in the form of an extract. When in the form of an extract any suitable solvent may be used, for example an aqueous solvent, such as water, or an organic solvent, such as ethanol, acetone or dichloromethane. In one embodiment, the kernel is used in the form of an extract in water. In an alternative embodiment, the kernel is used in the form of an extract in ethanol.

In one embodiment, all soluble components from the loquat kernel are used; in particular all water-soluble components and/or all ethanol-soluble components from the loquat kernel may suitably be used.

The loquat kernel may be used in the form of an extract, preferably an extract in water, that has a zero or substantially zero concentration of volatiles; in particular the extract may suitably have had all or substantially all volatiles removed.

In an alternative embodiment, the loquat kernel is used in ground form. In this embodiment, the kernel may have been ground to any suitable size. Preferably, the kernel has been ground to pass through a 5 mm sieve, more preferably a 2 mm sieve, most preferably a 1 mm sieve.

However, it is preferred that the kernel has not been ground too finely, as such a material would decompose relatively rapidly and therefore would be less effective; it is therefore preferred that 50% or more of the ground kernel would not pass through a 0.05 mm sieve; more preferably 60% or more, such as 70% or more, for example 80% or more. In one embodiment, the kernel has been ground such that 50% or more of the ground kernel will not pass through a 0.1 mm sieve; more preferably 60% or more, such as 70% or more, for example 80% or more.

The loquat kernel may be used in any suitable amounts or concentrations; clearly the amount used should be selected appropriately depending upon the intended application.

When considered on a wt/v basis, the loquat kernel may suitably be used in concentrations of 10 g/l or more, preferably 15 g/l or more, more preferably 20 g/l or more, most preferably 25 g/l or more, for example 30 g/l or more.

When considered on a wt/wt basis, the loquat kernel may suitably be used in concentrations of 10 g/kg or more, preferably 15 g/kg or more, more preferably 20 g/kg or more, most preferably 25 g/kg or more, for example 30 g/kg or more.

The invention further provides, in a second aspect, a method of killing, inactivating or repelling nematodes, which method comprises providing loquat kernel and applying the loquat kernel to the nematodes or to an area where the nematodes are likely to exist or to an area to where the nematodes are expected to move.

Suitably the method comprises providing the loquat kernel in ground, chopped, freeze dried or spray dried form or in the form of an extract. When provided in the form of an extract any suitable solvent may be used; for example an aqueous solvent, such as water, or an organic solvent, such as ethanol, acetone or dichloromethane. In one embodiment, the kernel is provided in the form of an extract in water. In an alternative embodiment, the kernel is provided in the form of an extract in ethanol.

Suitably, all soluble components from the loquat kernel may be provided, in particular all water-soluble components and/or all ethanol-soluble components from the loquat kernel may suitably be provided.

In one embodiment the loquat kernel is provided in the form of an extract, such as an extract in water, from which all or substantially all volatiles have been removed.

In an alternative embodiment, the loquat kernel is provided in ground form.

The method may suitably comprise the steps of providing loquat kernel, taking an extract thereof and applying the loquat kernel extract to the nematodes or to an area where the nematodes are likely to exist or to an area to where the nematodes are expected to move.

In particular, the step of taking an extract of the loquat kernel may comprise taking an extract of the kernel with water or with ethanol.

The method may further comprise the step of removing all or substantially all volatiles from the extract before the step of applying the extract.

The method may alternatively comprise the steps of providing loquat kernel, grinding it and applying the ground loquat kernel to the nematodes or to an area where the nematodes are likely to exist or to an area to where the nematodes are expected to move.

The kernel may be ground to any suitable size. Preferably, the kernel is ground to pass through a 5 mm sieve, more preferably a 2 mm sieve, most preferably a 1 mm sieve.

However, it is preferred that the kernel is not ground too finely, as such a material would decompose relatively rapidly and therefore would be less effective; it is therefore preferred that 50% or more of the ground kernel would not pass through a 0.05 mm sieve; more preferably 60% or more, such as 70% or more, for example 80% or more. In one embodiment, the kernel is ground such that 50% or more of the ground kernel will not pass through a 0.1 mm sieve; more preferably 60% or more, such as 70% or more, for example 80% or more.

The loquat kernel may be applied in any suitable amounts or concentrations; clearly the amount used should be selected appropriately depending upon the intended application.

When considered on a wt/v basis, the loquat kernel may suitably be applied in concentrations of 10 g/l or more, preferably 15 g/l or more, more preferably 20 g/l or more, most preferably 25 g/l or more, for example 30 g/l or more.

When considered on a wt/wt basis, the loquat kernel may suitably be applied in concentrations of 10 g/kg or more, preferably 15 g/kg or more, more preferably 20 g/kg or more, most preferably 25 g/kg or more, for example 30 g/kg or more.

Preferably, the nematodes are plant parasitic nematodes, for example root knot nematodes such as *Meloidogyne* spp.

It is preferred that the method is a method for selectively killing plant parasitic nematodes.

It is preferred that the method is a method for selectively killing nematodes over fungi.

The method may suitably involve applying loquat kernel to a growing medium, such as soil, peat, sand or water, in an area where nematodes are believed to exist or to a growing medium, such as soil, peat, sand or water, in an area to where nematodes are expected to move. For example, the loquat kernel may be applied to or mixed with a growing medium, such as soil, peat, sand or water, that is to have plants planted in it or may be applied to or mixed with a growing medium, such as soil, peat, sand or water, that has plants planted in it, especially when the plants are those that are vulnerable to nematodes.

The invention further provides, in a third aspect, a pesticide comprising loquat kernel and a pesticidally acceptable solvent, carrier, excipient or diluent.

The pesticide may suitably comprise all soluble components of loquat kernel, in particular all water-soluble components and/or all ethanol-soluble components of loquat kernel.

Suitably, the pesticide comprises, when considered on a wt/v basis, 10 g/l of loquat kernel or more, preferably 15 g/l or more, more preferably 20 g/l or more, most preferably 25 g/l or more, for example 30 g/l or more.

When considered on a wt/wt basis, the pesticide suitably comprises 10 g/kg of loquat kernel or more, preferably 15 g/kg or more, more preferably 20 g/kg or more, most preferably 25 g/kg or more, for example 30 g/kg or more.

The pesticide may comprise the kernel in ground, chopped, freeze dried or spray dried form or in the form of an extract. When in the form of an extract, any suitable solvent may be used, for example an aqueous solvent such as water or an organic solvent such as ethanol, acetone or dichloromethane. In one embodiment, the pesticide comprises an extract of loquat kernel in a pesticidally acceptable solvent, carrier, excipient or diluent. Preferably, the pesticide comprises an extract of loquat kernel in water.

In one particular such embodiment, the pesticide comprises an extract of loquat kernel, preferably an extract in water, that has a zero or substantially zero concentration of volatiles. In particular the pesticide may comprise an extract of loquat kernel, preferably an extract in water, that has had all or substantially all volatiles removed.

In an alternative embodiment, the pesticide comprises loquat kernel in ground form. In this embodiment, the kernel may have been ground to any suitable size. Preferably, the kernel has been ground to pass through a 5 mm sieve, more preferably a 2 mm sieve, most preferably a 1 mm sieve.

However, it is preferred that the kernel has not been ground too finely, as such a material would decompose relatively rapidly and therefore would be less effective; it is therefore preferred that 50% or more of the ground kernel would not pass through a 0.05 mm sieve; more preferably 60% or more, such as 70% or more, for example 80% or more. In one embodiment, the kernel has been ground such that 50% or more of the ground kernel will not pass through a 0.1 mm sieve; more preferably 60% or more, such as 70% or more, for example 80% or more.

The present invention also provides, in a fourth aspect, a method of producing a pesticide, which method comprises providing ground, chopped, freeze dried or spray dried loquat kernel.

In one embodiment, the method comprises providing ground loquat kernel. In this embodiment, the kernel may have been ground to any suitable size. Preferably, the kernel has been ground to pass through a 5 mm sieve, more preferably a 2 mm sieve, most preferably a 1 mm sieve.

However, it is preferred that the kernel has not been ground too finely, as such a material would decompose relatively rapidly and therefore would be less effective; it is therefore preferred that 50% or more of the ground kernel would not pass through a 0.05 mm sieve; more preferably 60% or more, such as 70% or more, for example 80% or more. In one embodiment, the kernel has been ground such that 50% or more of the ground kernel will not pass through a 0.1 mm sieve; more preferably 60% or more, such as 70% or more, for example 80% or more.

In one particular such embodiment, the step of providing ground loquat kernel comprises the sub steps of providing loquat kernel and then grinding the kernel.

In one embodiment, the method comprises providing ground loquat kernel and further comprises the step of taking extracts of the ground loquat kernel. Any suitable solvent may be used to take the extract, for example an aqueous solvent, such as water, or an organic solvent, such as ethanol, acetone or dichloromethane. In particular, the method may comprise the further step of taking extracts in water or extracts in ethanol of the ground loquat kernel.

The method may further comprise the step of removing all or substantially all volatiles from the ground kernel extract.

In one particular such embodiment, the step of providing ground loquat kernel comprises the sub steps of providing loquat kernel and then grinding the kernel.

The invention will now be further described, for the purposes of illustration only, in the following examples.

BRIEF DESCRIPTIONS OF THE DRAWINGS

EXAMPLES

Figure 1:
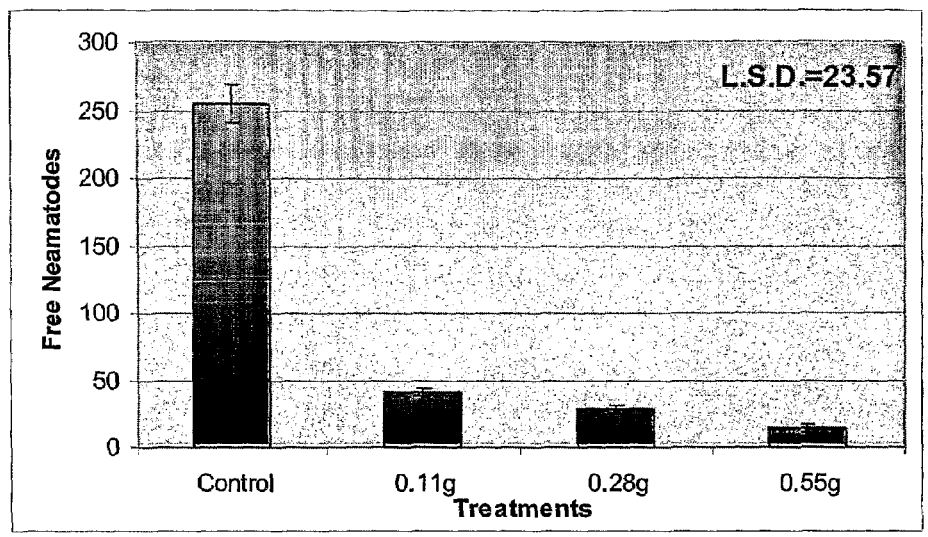
FIG. 1 is a graph showing the results for different levels of treatment with ground loquat kernel.

Water extracts from Moraira loquat kernels (Algerie or Cardona varieties) were evaluated in a number of experiments. The stock solution used in each case was prepared by 5 g ground kernels (fresh weight) being extracted in Soxflo™ with 50 ml distilled water.

Example 1

Experiments With Juvenile Root-knot Nematodes

The water extracts were tested against plant parasitic nematodes, *Meloidogyne* spp. This root knot nematode is a major crop pest.

Juvenile root-knot nematodes were exposed to different concentrations of the stock solution.

Method:

Two Stock Solutions were prepared as above. One was prepared and stored in the fridge for a month (Stock A) and the other was produced and used immediately (Stock B). Nematodes were then treated with 90, 50 and 10% concentrations of these Stock Solutions (e.g. for a 90% concentration the ratio of stock solution: water was 9:1, v/v). Equivalent controls were left in water.

After treatment the nematodes were placed in water to observe any recovery.

Results:

The product inactivated the nematodes immediately.

| | Root Knot Nematodes (using Stock B) | | | |
|---|---|---|---|---|
| | % Inactivation after initial application | | | |
| Concentration | Replicate 1 | Replicate 2 | Replicate 3 | Average Inactivation(%) |
| 90% solution | 100 | 100 | 100 | 100.0 |
| 50% solution | 100 | 100 | 100 | 100.0 |
| 10% solution | 100 | 100 | 99.5 | 99.8 |
| 90% Control | 0 | 0 | 0 | 0.00 |
| 50% Control | 0 | 0 | 0 | 0.00 |
| 10% Control | 0 | 0 | 0 | 0.00 |

| | Root Knot Nematodes (Using Stock A) | | | |
|---|---|---|---|---|
| Concentration | % Inactivation after initial application | | | Average inactivation (%) |
| 90% solution | 100 | 100 | 100 | 100.0 |
| 50% solution | 100 | 100 | 100 | 100.0 |
| 10% solution | 99 | 100 | 100 | 99.5 |
| 90% Control | 0 | 0 | 0 | 0.00 |
| 50% Control | 0 | 0 | 0 | 0.00 |
| 10% Control | 0 | 0 | 0 | 0.00 |

When the nematodes were returned to fresh water and observed for 22 hours, only those that had been inactivated by the 10% solution recovered.

Conclusion:

The solutions killed root-knot nematodes at 50% and 90% concentration, but at 10% inactivation was reversible.

Example 2

Further Experiments With Juvenile Root-knot Nematodes

Method:

Example 1 was repeated but using 40, 30, and 20% solutions.

Results:

The same results as in Example 1 were obtained. No recovery occurred when nematodes were replaced in water.

Conclusion:

The concentration of Solution at which there is inactivation with no recovery is between 10 and 20%.

In further repeat studies the period of observation of recovery was extended to 8 days (instead of 22 hours as above). No significant recovery was recorded with the 40, 30, and 20% solutions.

Example 3

The Efficacy of the Product on Inactivation of Root-knot Nematodes After Storage Method:

Two different batches of Stock Solution prepared as above were tested to compare whether any loss of efficacy had occurred over time. Stock C was stored in the fridge at 5° C. for a month after preparation; Stock D was freshly prepared from ground kernels that had been stored in the freezer before use. The time it took for the root-knot nematodes to become inactivated by the product was compared for the two batches. Two concentrations, 90% and 50%, and a water control were evaluated.

Result:

Both concentrations of both Stock C and Stock D caused instantaneous paralysis to the root-knot nematodes.

Conclusion:

Efficacy was not lost during storage of the product at 5° C.

Example 4

The Role of the Volatile Compounds in the Moraira Kernels

Experiments were carried out to determine whether volatile compounds in the kernels are the principles that kill the nematodes.

Method:
Experiments were conducted under conditions as described above, but in one treatment lids of containers were removed (to allow volatiles to escape). Dosages were 50, 40, 30 and 20% of the above Stock Solution.

Results:
The nematodes were observed over 3 days. In both treatments (with or without lid) and at all concentrations the nematodes ceased to move [indicated by (X)]. Controls remained active (data not shown)

| | Experiment with lid | | | | | | | | | | | |
|---|---|---|---|---|---|---|---|---|---|---|---|---|
| | Day | | | Day | | | Day | | | Day | | |
| | 1 | 2 | 3 | 1 | 2 | 3 | 1 | 2 | 3 | 1 | 2 | 3 |
| 50% | X | X | X | 40% X | X | X | 30% X | X | X | 20% X | X | X |

| | Experiment without lid | | | | | | | | | | | |
|---|---|---|---|---|---|---|---|---|---|---|---|---|
| | Day | | | Day | | | Day | | | Day | | |
| | 1 | 2 | 3 | 1 | 2 | 3 | 1 | 2 | 3 | 1 | 2 | 3 |
| 50% | X | X | X | 40% X | X | X | 30% X | X | X | 20% X | X | X |

Conclusion:
The results suggest that the active principles are not all volatiles.

The work was then repeated using solutions from which the volatiles had been removed. The same results were shown, which suggests that there are non-volatile compounds in the water extract that will kill root-knot nematodes.

Example 5

The Activity of the Water Extract Against Non-plant Parasitic Nematodes

Experiments were carried out to determine whether the water extracts are active on all types of nematodes, or whether they show some selectivity against different types of nematodes.

Method:
I. Nematodes that feed on bacteria are common soil inhabitants. Some of these nematodes of the genus *Steinernema* were exposed to a 50% solution of the Stock Solution.
II. A field-collected mixed population of all trophic groups of nematodes (fungus-feeding, bacteria-feeding, predatory and plant parasitic) was exposed to a 50% solution of the Stock Solution.

Results:
I. The *Steinernema* nematodes were not inactivated.
II. Of the mixed population all the plant parasites were inactivated. Some of the non-plant parasites were still active, this probably varied across trophic groups.

Conclusion:
Nematodes with different feeding behaviours are affected differently by the product. All plant parasitic nematodes were inactivated.

Example 6

Activity Against Larvae of the Wax Moth *Galleria Mellonella*

The wax moth *Galleria mellonella* is a standard laboratory test insect and such moths are readily mass-produced in the laboratory or can be bought from a supplier, e.g. Live Foods Direct.

Methods:
In several studies larvae (larvae either of different stages or only $1^{st}$ instar larvae) were exposed to the product by direct application. Observations continued over 36 days.

Results:
The product did not show activity when applied to the larvae. Development to adult progressed although in some preliminary tests the water extract appeared to halt development. The experiment as repeated with $1^{st}$ instar larvae showed no effect.

Example 7

Activity Against Some Beneficial Insects

The wasp *Encarsia formosa*, parasitic on whiteflies, the predacious mite *Phytoseiulus persimilis* that preys on spider mites and nymphs and adults of the thrip predator *Amblyseius cucumeris* (all bought from a biological control company) were exposed to the Stock Solution.

Results:

There was no mortality.

Example 8

Activity Against a Pathogenic Fungus

Method:

The Stock Solution was tested at full strength against two isolates of the root-infecting fungus *Pythium aphanideratum*.

Plugs of actively growing fungus were placed on water-agar in Petri plates; drops of 25 and 50 microliters of the product were placed in different positions around the fungus. Growth of the fungus was monitored over 48 h at 25° C. Sterile water drops were used as controls.

Result:

Growth of the fungus was not inhibited.

Example 9

Activity Testing of Loquat Kernels in a Water Screen

Method:

100 microliters containing nematodes were pipetted into 2.5 cm Petri dishes. The nematodes used were principally root-knot nematodes (*Meloidogyne* sp) but some initial observations were also made on some *Pratylenchus* sp. and free-living species (non-plant parasites). 900 microliters of Loquat extract, or 500 microliters of Loquat extract plus 400 microliters of water, were added to the nematodes to give concentrations of 90 or 50% of the original Loquat extract. Total added volume was therefore 1 ml. Comparable experiments using amygdalin solution instead (solutions made from (a) 70 mg dissolved in 50 ml water and (b) 400 mg dissolved in 50 ml water) were also carried out.

Controls were nematodes from the same source placed in tap water.

Following application of the Loquat or amygdalin solution, observations were made after 10 minutes, the next day, and after 5 days.

Results:

10 minutes after application:

No movement of plant parasitic nematodes observed at either concentration of Loquat kernels; but free-living nematodes remained active.

Amygdalin: all nematodes still active at both concentrations after 10 minutes.

Next day:

No movement of the plant parasitic nematodes at either concentration of Loquat kernels.

Nematodes in both amygdalin treatments were active.

5 days later:

Same results: no movement in Loquat kernel extracts; but nematodes still active in both amygdalin treatments.

Conclusions:

Loquat kernels in the water screen cause plant parasitic nematodes to be killed, but free living, beneficial nematodes are not damaged.

However, amygdalin itself is not active per se.

Example 10

Pot Experiments With Nematodes and Plants in Greenhouse

Method:

Ground kernels were thoroughly mixed into John Innes No.2 loam based compost (33 g). Doses applied were 0.33, 0.83, 1.66 g per pot and an untreated control.

Four-week old tomato plants cv Tiny Tim were planted into the amended soil and approximately 700 root-knot nematode juveniles were then inoculated.

Plants were left to grow in a heated glasshouse at 20° C. (+/−5° C.). After 48 days plants were washed from the pots; fresh weights of foliage and root systems were taken; numbers of root-knot nematode egg masses per root system were recorded.

Results:

| Treatment level | | Root weight | Shoot weight | Gall index | Total egg masses | Egg masses/ g root |
|---|---|---|---|---|---|---|
| Control | 1 | 1.84 | 3.45 | 4 | 156 | 84.78 |
|  | 2 | 2.12 | 2.58 | 4 | 178 | 83.96 |
|  | 3 | 1.80 | 2.51 | 4 | 161 | 89.44 |
|  | 4 | 1.47 | 2.33 | 4 | 197 | 134.01 |
|  | Mean | 1.81 | 2.72 | 4.0 | 173 | 98.05 |
| 0.33 g | 1 | 2.51 | 2.57 | 3 | 200 | 79.68 |
|  | 2 | 2.07 | 3.08 | 4 | 198 | 95.65 |
|  | 3 | 3.04 | 2.01 | 3 | 89 | 29.25 |
|  | 4 | 2.76 | 2.86 | 4 | 118 | 42.75 |
|  | Mean | 2.60 | 2.63 | 3.5 | 151 | 61.83 |
| 0.83 g | 1 | 1.28 | 2.09 | 3 | 104 | 81.25 |
|  | 2 | 2.16 | 2.22 | 4 | 112 | 51.85 |
|  | 3 | 1.74 | 2.39 | 4 | 68 | 39.08 |
|  | 4 | 1.77 | 2.48 | 4 | 140 | 79.09 |
|  | Mean | 1.74 | 2.30 | 3.8 | 106 | 62.82 |
| 1.66 g | 1 | 0.81 | 2.14 | 2 | 38 | 46.91 |
|  | 2 | 1.43 | 1.93 | 3 | 30 | 20.98 |
|  | 3 | 1.75 | 2.75 | 2 | 28 | 16.00 |
|  | 4 | 1.72 | 2.48 | 2 | 98 | 56.98 |
|  | Mean | 1.43 | 2.33 | 2.3 | 49 | 35.22 |

Conclusions:

Significantly fewer egg masses were produced on plants treated with the highest dose. This would confirm that there are nematicidal compounds in the Loquat seeds.

The product also appears somewhat phytotoxic and this was reflected in lower root weights and in the slightly stunted shoots.

Example 11

Effect of Ground Kernels on Nematodes in Soil

Method:

30 cm$^3$ of air dried John Innes loam based compost was treated with 0.11, 0.28 and 0.55 g of ground kernel in plastic containers. Each was then inoculated with 600 root-knot nematodes contained in 1 ml water and a further 7 ml water was added to provide adequate moisture. After 48 h nematodes were extracted from the soil using the conventional incubation technique over 24 h. The treatments had four replicates.

Results:

FIG. 1 is a graph showing the results for the different levels of treatment.

Conclusions:

All Loquat treatments had a significant effect on the recovery of nematodes from the soil indicating that the kernel powder had inactivated the nematodes during the 48 h period.

Example 12

Dipping Tomato Plants in Aqueous Loquat Extract

Method:

Two-week old tomato plants were dipped for 1 h in Loquat extracts of 25, 50, and 75% of the original stock material. The treated plants were then planted into soil (John Innes No2 loam-based compost) and inoculated with 375 root-knot nematodes. The plants were then grown in the glasshouse for 1 month when nematode development was assessed.

Figure 2:
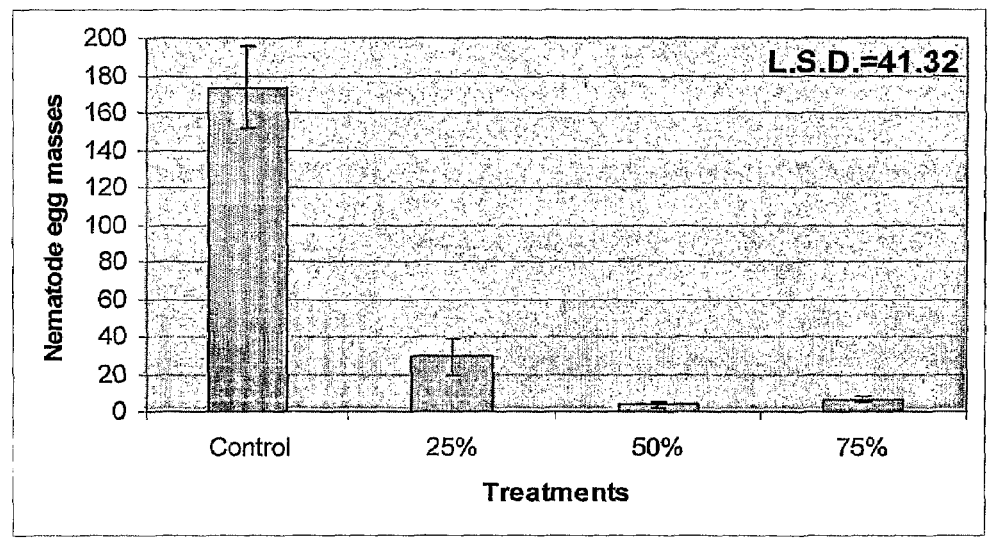
FIG. 2 is a graph showing the results for different levels of treatment with loquat extract.

Result:

FIG. 2 is a graph showing the results for the different levels of treatment.

Conclusions:

The effect of dipping the tomato root systems in all concentrations of the extract prevented invasion by the root-knot nematodes. This suggests that the toxic effects of the extract were sufficiently persistent to prevent nematodes invading.

The invention claimed is:

1. A method of killing, inactivating or repelling root knot nematodes, which comprises the addition of an effective amount of loquat kernel to nematodes or a growing medium.

2. A method according to claim 1, wherein the loquat kernel is used as a nematicide.

3. A method according to claim 2, wherein the loquat kernel is used as a selective nematicide for root knot nematodes.

4. A method according to claim 1, wherein the loquat kernel is used as a selective treatment for root knot nematodes over fungi.

5. A method according to claim 1, wherein the loquat kernel is used in ground, chopped, freeze dried or spray dried form or in the form of an extract.

6. A method according to claim 5, wherein the kernel is used in the form of an extract in water.

7. A method according to claim 5, wherein the kernel is used in the form of an extract in an organic solvent.

8. A method according to claim 7, wherein the solvent is ethanol.

9. A method according to claim 1, wherein all soluble components from the loquat kernel are used.

10. A method according to claim 1, wherein all water-soluble components from the loquat kernel are used.

11. A method according to claim 1, wherein all organic solvent-soluble components from the loquat kernel are used.

12. A method according to claim 1, wherein all ethanol-soluble components from the loquat kernel are used.

13. A method according to claim 5, wherein the loquat kernel is in ground form.

14. A method according to claim 13, wherein the kernel has been ground so as to pass through a 5 mm sieve but such that 50% or more of the ground kernel would not pass through a 0.1 mm sieve.

15. A method of killing, inactivating or repelling root knot nematodes, which method comprises providing loquat kernel and applying the loquat kernel to the nematodes or to a growing medium.

16. The method of claim 15, wherein the method comprises providing the loquat kernel in ground, chopped, freeze dried or spray dried form or in the form of an extract.

17. The method of claim 16, wherein the method comprises providing the kernel in the form of an extract in water.

18. The method of claim 16, wherein the method comprises providing the kernel in the form of an extract in an organic solvent.

19. The method according to claim 18, wherein the solvent is ethanol.

20. The method according to claim 15, wherein all soluble components from the loquat kernel are provided.

21. The method of claim 16, wherein the loquat kernel is provided in ground form.

22. The method of claim 15, wherein the method comprises applying loquat kernel to a growing medium.

23. The method of claim 22, wherein the loquat kernel is applied to or mixed with a growing medium that is to have plants planted in it or is applied to or mixed with a growing medium that has plants planted in it.

* * * * *